(12) United States Patent
Lee

(10) Patent No.: US 8,336,114 B1
(45) Date of Patent: Dec. 25, 2012

(54) PROTECTIVE MASK

(76) Inventor: Shih-Min Lee, Taoyuan County (TW)

( * ) Notice: Subject to any disclaimer, the term of this patent is extended or adjusted under 35 U.S.C. 154(b) by 0 days.

(21) Appl. No.: 13/208,536

(22) Filed: Aug. 12, 2011

(51) Int. Cl.
*A61F 9/04* (2006.01)

(52) U.S. Cl. .............................................. 2/9

(58) Field of Classification Search ............. 2/427, 431, 2/448, 449, 450, 451, 452, 453, 9
See application file for complete search history.

(56) References Cited

U.S. PATENT DOCUMENTS

| | | | | |
|---|---|---|---|---|
| 2,283,120 A * | 5/1942 | Malcom | | 2/8.1 |
| 2,360,101 A * | 10/1944 | Bowers | | 2/8.1 |
| 3,047,876 A * | 8/1962 | Malcom, Jr. | | 2/9 |
| 3,074,072 A * | 1/1963 | Edwards et al. | | 2/8.1 |
| 3,075,201 A * | 1/1963 | Lindblom | | 2/8.1 |
| 3,079,609 A * | 3/1963 | Hoffmaster | | 2/8.1 |
| 3,430,263 A * | 3/1969 | Newcomb | | 2/8.1 |
| 4,040,123 A * | 8/1977 | Williams | | 2/10 |
| 4,464,800 A * | 8/1984 | Edwards | | 2/452 |
| 4,536,892 A * | 8/1985 | Brinkhoff et al. | | 2/424 |
| 5,077,836 A * | 1/1992 | Idoff et al. | | 2/10 |
| 5,337,419 A * | 8/1994 | Russell | | 2/9 |
| 5,571,217 A * | 11/1996 | Del Bon et al. | | 2/9 |
| 6,154,881 A * | 12/2000 | Lee | | 2/9 |
| 6,260,197 B1 * | 7/2001 | Hoogewind | | 2/8.3 |
| 7,120,939 B1 * | 10/2006 | Howard et al. | | 2/416 |
| 8,161,576 B2 * | 4/2012 | Lemke et al. | | 2/418 |
| 2006/0080761 A1 * | 4/2006 | Huh | | 2/424 |

* cited by examiner

*Primary Examiner* — Danny Worrell
(74) *Attorney, Agent, or Firm* — Rosenberg, Klein & Lee

(57) ABSTRACT

A protective mask is revealed. The protective mask includes a mask body, a hoop mounted in the mask body, two angle adjustment members, and a head size adjustment device. The mask body is pivoted to the hoop and the hoop is adjusted by the head size adjustment device on a rear side of the mask body so as to fit head size of users. While being lifted, the angle of the mask body is adjusted and positioned by the angle adjustment members on left and right sides of the mask body. Thereby the protective mask can be applied to users with various head sizes. The users can wear the protective mask firmly and comfortably. Moreover, the angle adjustment of the protective mask is more convenient and simpler.

3 Claims, 9 Drawing Sheets

PROTECTIVE MASK

BACKGROUND OF THE INVENTION

1. Field of the Invention

The present invention relates to a protective mask, especially to a protective mask in which a hoop is adjusted to become tighter or looser for fitting user's head circumference. Moreover, a mask body of the protective mask can be rotated and lifted to a certain angle for meeting requirements of various users.

2. Description of Related Art

Generally, an industrial safety mask includes a lens for faces protection of users. For example, a welding safety mask is used to protect users from bright light and sparks generated during the welding process. The design of the safety mask includes a lens and a mask body, both being arranged with through holes one two sides thereof. By screws inserted into the through holes, the lens and the mask body are pivoted and connected to each other. When users intend to lift the lens, the screws on two sides are loosened and the lens is adjusted to the position required. Then the screws on two sides are threaded and tightened. The repeated steps of rotating to loosen, adjustment and threading to tighten cause inconvenience in use. Moreover, users may lift or pull the mask down without proper operation and the screws are not correctly placed. Thus the lens already lifted may fall down sometimes.

Moreover, most of safety masks are with fixed size. Thus for users whose head size is larger or smaller, the only way to have a tight fit is by means of a fastener underneath the chin. Thus the safety mask will not fall off from user's head. This leads to discomfort of wearing. After wearing for a long period of time, users may feel uncomfortable on cheek and chin area. Therefore, there is room for improvement.

SUMMARY OF THE INVENTION

Therefore it is a primary object of the present invention to provide a protective mask in which a hook can be rotated and adjusted to become tighter or looser for fitting user's head size. Moreover, a mask body of the protective mask can be rotated and lifted to different angles according to requirements of various operations.

In order to achieve the above object, a protective mask of the present invention includes a mask body, a hoop received in the mask body, two angle adjustment members, and a head size adjustment device. The mask body consists of a hollow frame curved inward, and a lens arranged at a concave area of the hollow frame. An insertion hole is disposed on each of two sides of the hollow frame correspondingly. A curved part is disposed on a front end of the hoop and two head circumference pieces extend horizontally from two ends of the curved part respectively. A slot is formed on a rear end of each head circumference piece 22. A plurality of locking teeth is arranged at one side of each slot. A fastening segment and a corresponding adjustment segment are respectively extending upwards from one end of the curved part. A positioning ring corresponding to the insertion hole is disposed projectingly on each of two ends of the curved part. The mask body is pivoted to the hoop by the two positioning rings and a plurality of holes is arranged around an outer surface of each positioning ring. Then each angle adjustment member is inserted through the insertion hole of the mask body and the positioning ring of the hoop so as to adjust position and angle of the mask body by rotation of the angle adjustment member. From outside to inside, the angle adjustment member consists of a side knob, a projective pivot shaft arranged at an inner side of the side knob and passing through the insertion hole and the positioning ring, an elastic part disposed around the pivot shaft, a positioning disc with a plurality of projecting blocks around a circumference on an outer surface thereof, and a fixing block that is connected to the pivot shaft for placing the elastic part and the positioning disc around the pivot shaft. Next the head size adjustment device is rotated and fixed on the slots of the head circumference pieces. The head size adjustment device is composed of an inner housing, a first disc, an elastic element, a second disc, an outer housing and a rear knob from inside to outside. A shaft passing through the slot is disposed on an outer surface of the inner housing. A ratchet wheel engaged with the locking teeth is arranged at an inner surface of the first disc and a first projection for mounting the shaft is disposed on an outer surface of the first disc. The elastic element is placed around the first projection and then to be locked and connected to the second disc. A second projection for connection of the rear knob is arranged at an outer surface of the second disc and a plurality of positioning bumps is disposed around the circumference of the second disc. The outer housing with a third disc on an outer surface thereof is assembled with the inner housing. The third disc is set with a plurality of concaves arranged circularly thereof and the concaves are corresponding to and locked with the positioning bumps.

Thereby the positioning bumps are released from the concaves of the third disc by pressing the rear knob. Then the rear knob is rotated to drive the second disc rotating. Thus the first disc locked in the second disc is also rotated and the ratchet wheel on the inner surface of the first disc make the two head circumference pieces tighter or looser until the protective mask fitting user's head size.

Moreover, the side knobs on both sides of the mask body are pressed to make the pivot shaft push the positioning disc. This leads to the releasing of the projecting blocks of each positioning disc from the holes of each positioning ring. Thus the users can lift the mask body to an angle or a proper position users required by rotating the side knobs.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
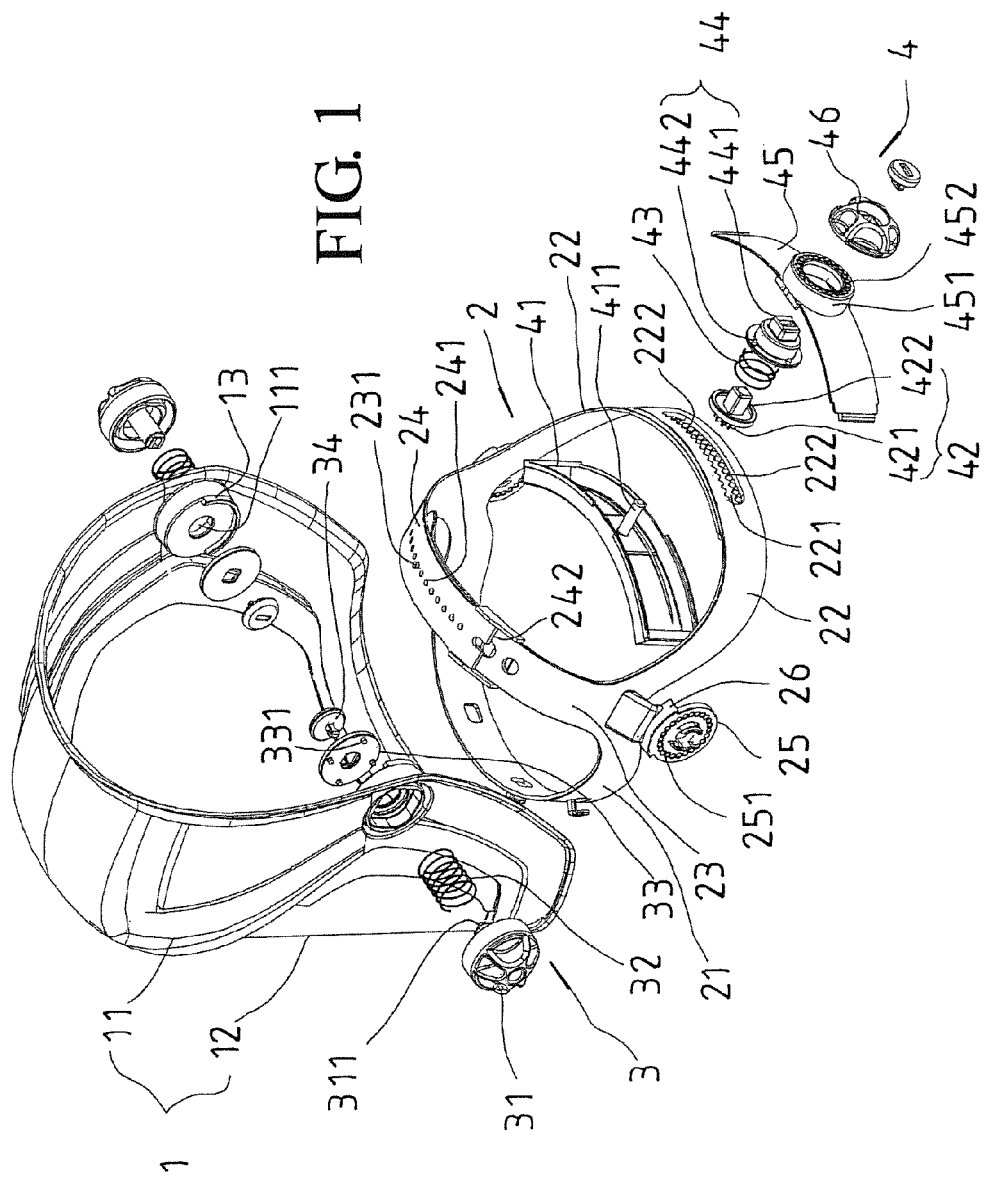
FIG. 1 is an explosive view of an embodiment according to the present invention.
Figure 2:
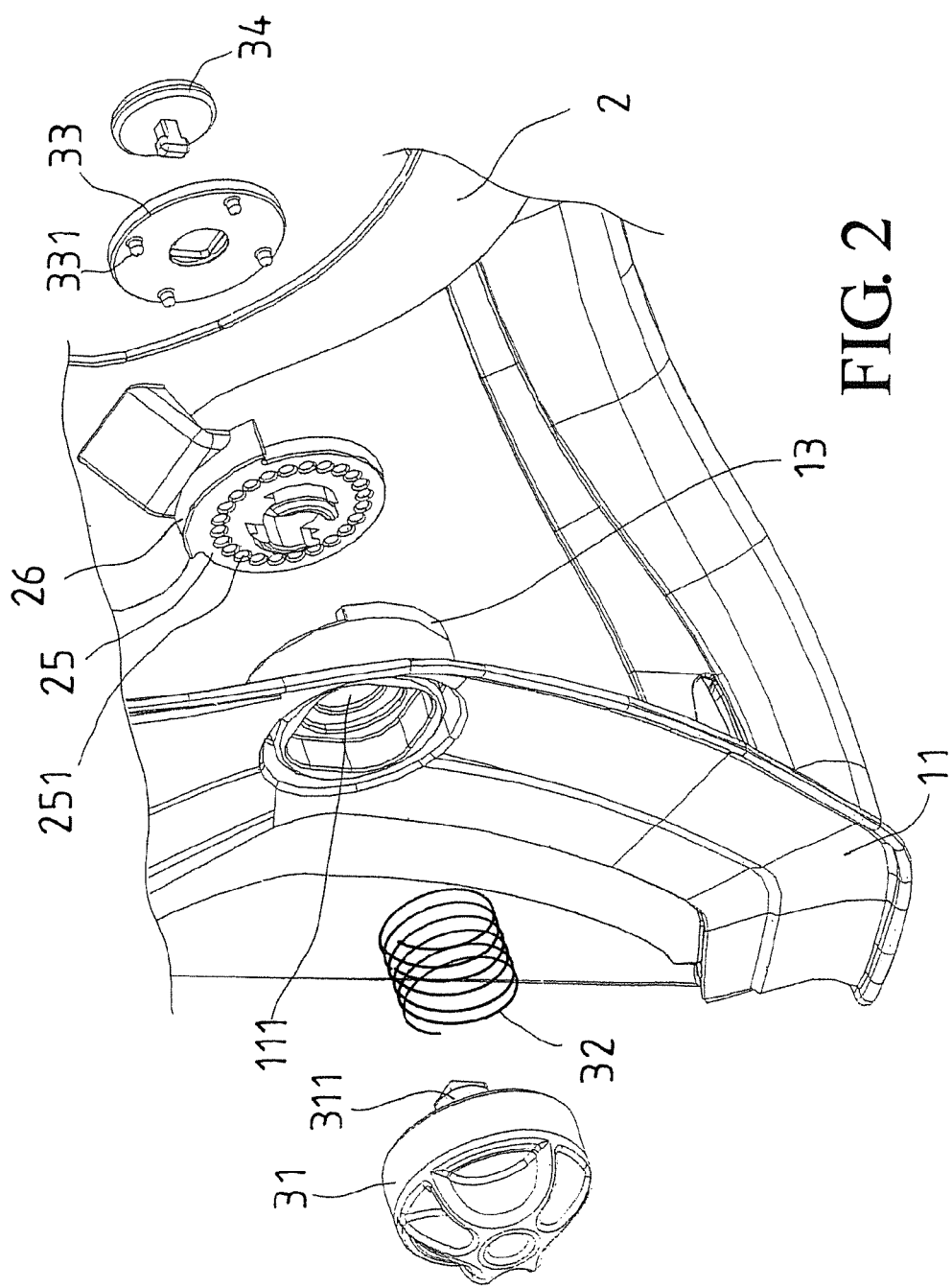
FIG. 2 is a partial enlarged explosive view of a hoop received in a mask body of an embodiment according to the present invention.

Refer to FIG. 1 and FIG. 2, a protective mask of the present invention includes a mask body 1, a hoop 2, two angle adjustment members 3, and a head size adjustment device 4.

The mask body 1 consists of a hollow frame 11 curved inward, and a lens 12 arranged at a concave area of the hollow frame 11. An insertion hole 111 is disposed on each of two sides, the left side and the right side, of the hollow frame 11 correspondingly.

The hoop 2 is received in the hollow frame 11. A curved part 21 is disposed on a front end of the hoop 2 and each of two head circumference pieces 22 extends horizontally from each of two ends of the curved part 21. A slot 221 is formed on a rear end of each head circumference piece 22. A plurality of locking teeth 222 is arranged at one side of each slot 221. A fastening segment 23 and a corresponding adjustment segment 24 are respectively extending upwards from one end of the curved part 21. By the fastening segment 23 and the adjustment segment 24 fastened with each other, a space inside the hoop 2 for receiving the head is adjusted. A positioning ring 25 corresponding to the insertion hole 111 is disposed projectingly on each of two ends of the curved part 21. The mask body 1 is pivoted to the hoop 2 by the two positioning rings 25 and a plurality of holes 251 is arranged around an outer surface of each positioning ring 25.

Each angle adjustment member 3 is inserted through the insertion hole 111 of the mask body 1 and the positioning ring 25 of the hoop 2. Thus the position and angle of the mask body 1 are adjusted by rotation of the angle adjustment member 3. From outside to inside, the angle adjustment member 3 includes a side knob 31, a projective pivot shaft 311 arranged at an inner side of the side knob 31 and passing through the insertion hole 111 and the positioning ring 25, an elastic part 32 disposed around the pivot shaft 311, a positioning disc 33 with a plurality of projecting blocks 331 around a circumference on an outer surface thereof, and a fixing block 34 that is connected to the pivot shaft 311 for placing the elastic part 32 and the positioning disc 33 around the pivot shaft 311.

The head size adjustment device 4 is rotated and fixed on the slots 221 of the head circumference pieces 22. From inside to outside, the head size adjustment device 4 includes an inner housing 41, a first disc 42, an elastic element 43, a second disc 44, an outer housing 45 and a rear knob 46. A shaft 411 that passes through the slot 221 is disposed on an outer surface of the inner housing 41. A ratchet wheel 421 engaged with the locking teeth 222 is arranged at an inner surface of the first disc 42 and a first projection 422 for receiving the shaft 411 is disposed on an outer surface of the first disc 42. The elastic element 43 is placed around the first projection 422 and then to be mounted and locked into the second disc 44. A second projection 441 for connection of the rear knob 46 is set on an outer surface of the second disc 44 and a plurality of positioning bumps 442 is disposed around the circumference of the second disc 44. The outer housing 45 and the inner housing 41 are assembled with each other. A third disc 451 with a plurality of concaves 452 arranged circularly thereof is arranged at an outer surface of the outer housing 45. The concaves 452 are corresponding to and locked with the positioning bumps 442.

Moreover, one side of the fastening segment 23 is disposed with a locking block 231 while the adjustment segment 24 is arranged with a plurality of locking holes 241 and a groove 242 on a rear end thereof. The locking block 231 is locked into one of the locking holes 241 and the fastening segment 23 is inserted through the groove 242. By the locking holes 241 of the adjustment segment 24, the space of the hoop 2 for mounting a user's head is adjusted.

Figure 3:
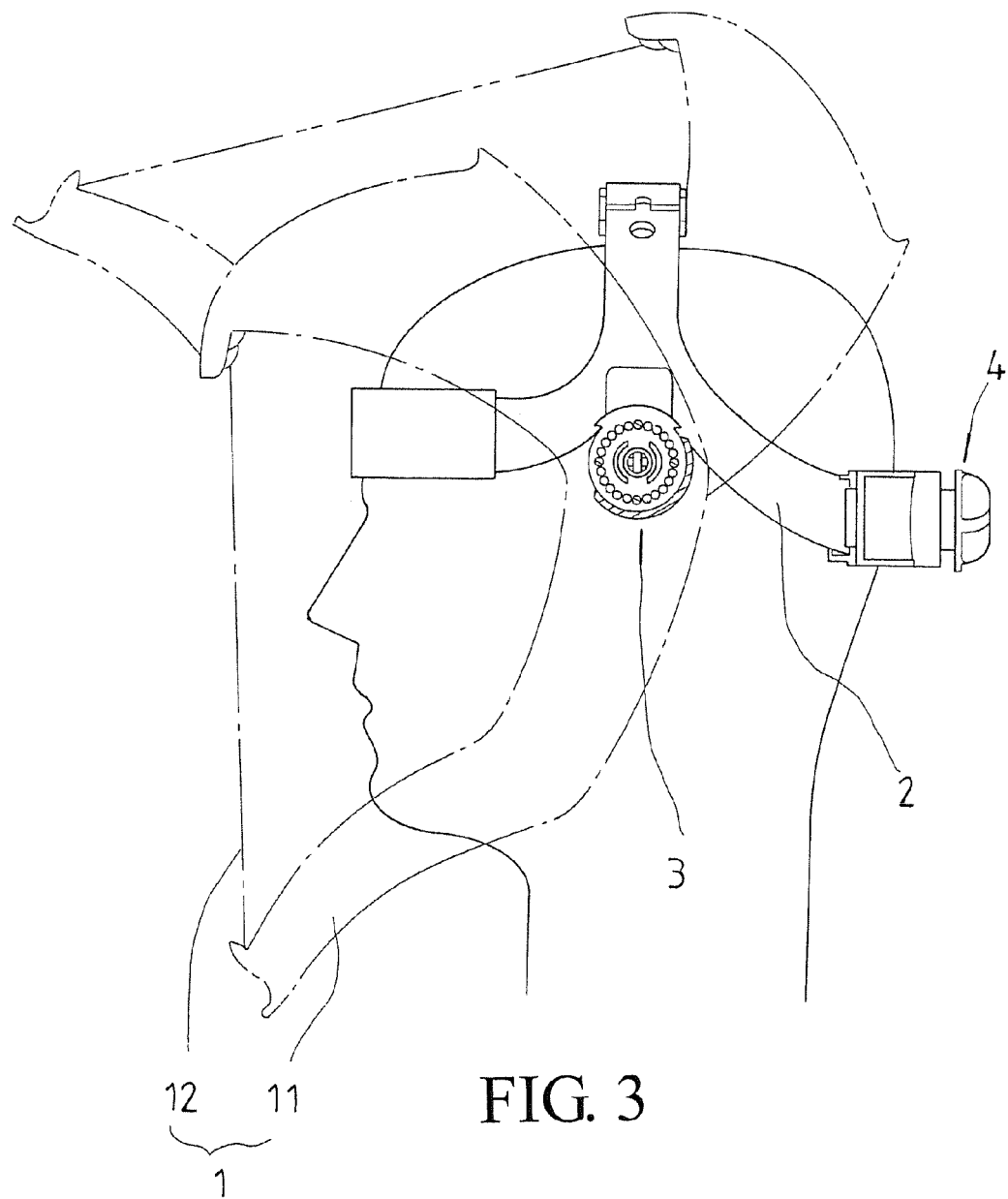
FIG. 3 is a side view of an embodiment in use according to the present invention.
Figure 4:
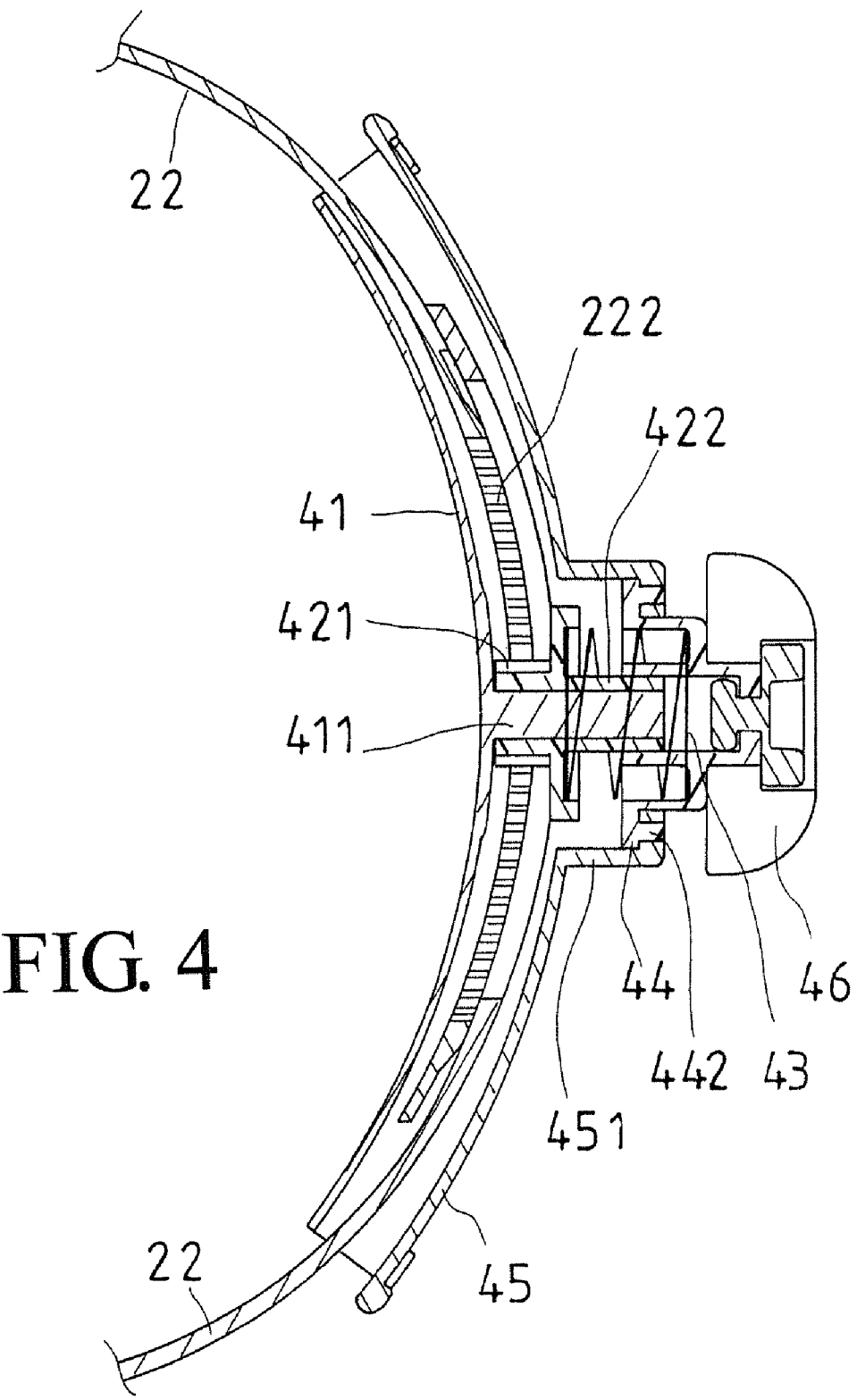
FIG. 4 is a cross sectional view of a rear knob of an embodiment without being pressed according to the present invention.
Figure 5:
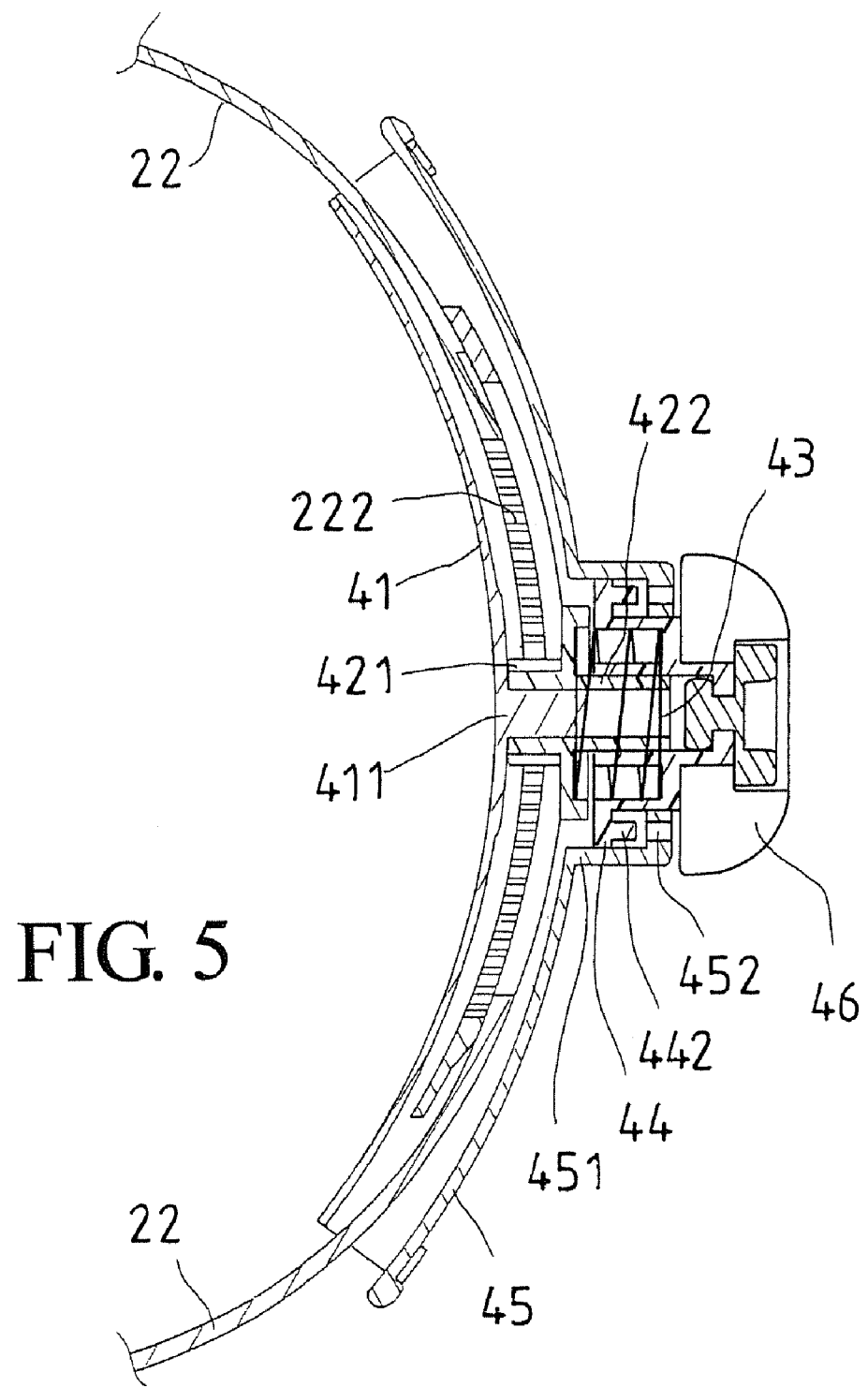
FIG. 5 is a cross sectional view of a rear knob of an embodiment being pressed according to the present invention.

In use, refer from FIG. 3 to FIG. 5, according to users' head size, the rear knob 46 is pressed to compress the elastic element 43 and the positioning bumps 442 are released from the concaves 452 of the third disc 451. Then the rear knob 46 is rotated so as to drive the second disc 44 rotating. Thus the first disc 42 locked in the second disc 44 is also rotated and the ratchet wheel 421 on the inner surface of the first disc 42 make the two head circumference pieces 22 tighter or looser. The length of the two head circumference pieces 22 relative to each other is adjusted. For example, when the rear knob 46 is rotated clockwise, the locking teeth 222 of the two slots 221 are moved and the two head circumference pieces 22 are respectively moved toward each other. Thus the hoop 2 is getting tighter and the head size mounted therein is smaller. On the other hand, while rotating the rear knob 46 counterclockwise, the locking teeth 222 of the two slots 221 are moved and the two head circumference pieces 22 are respectively moved away from each other so that the hoop 2 is looser for receiving larger head circumference.

Figure 6:
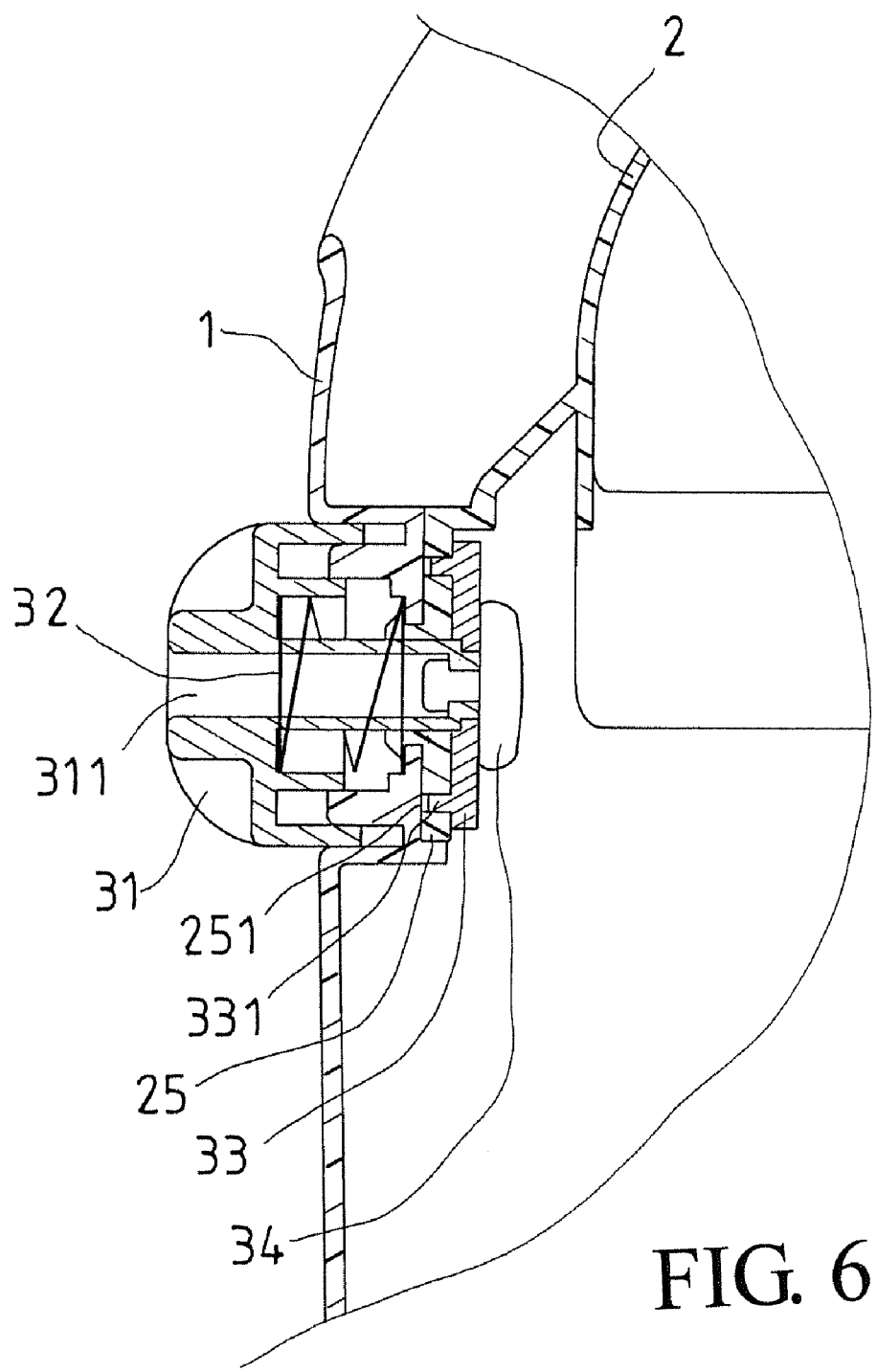
FIG. 6 is a cross sectional view of a left-side knob of an embodiment without being pressed according to the present invention.
Figure 7:
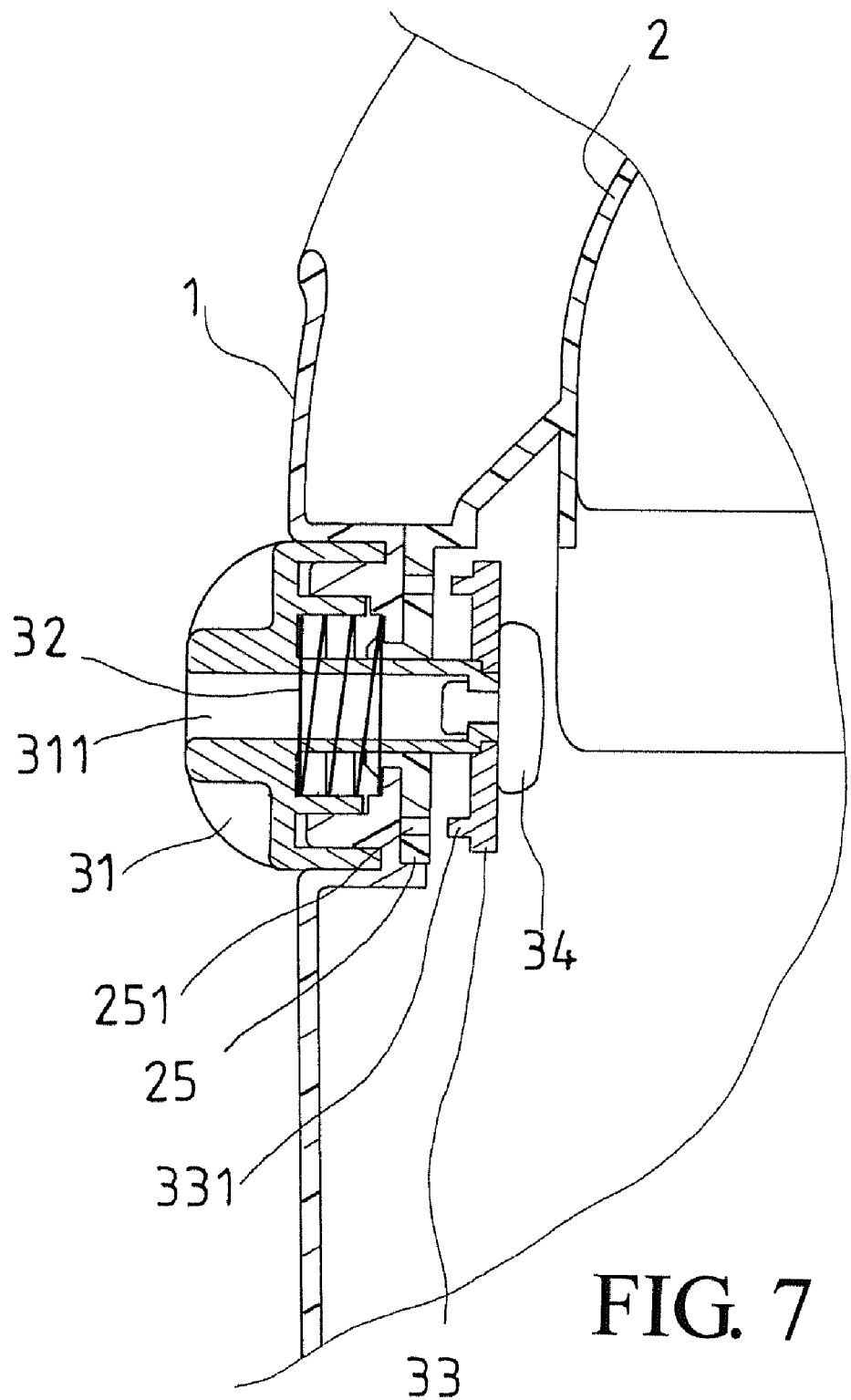
FIG. 7 is a cross sectional view of a left-side knob of an embodiment being pressed according to the present invention.

When users want to lift the mask body 1, refer to FIG. 6 and FIG. 7, the side knobs 31 on both sides of the mask body 1 are pressed simultaneously so as to make the projecting blocks 331 of each positioning disc 33 become released from the holes 251 of each positioning ring 25. This is due to that the positioning disc 33 is locked between the pivot shaft 311 of the side knob 31 and the fixing block 34. The two side knobs 31 are rotated and the mask body 1 is lifted to a proper position. When the side knobs 31 is released from being pressed, the projecting blocks 331 of each positioning disc 33 and the holes 251 of each positioning ring 25 are locked correspondingly by elastic recovery force of the elastic part 32. Thus the mask body 1 is unable to spin around the hoop 2. Therefore, the mask body 1 will not go down after being lifted.

Figure 8:
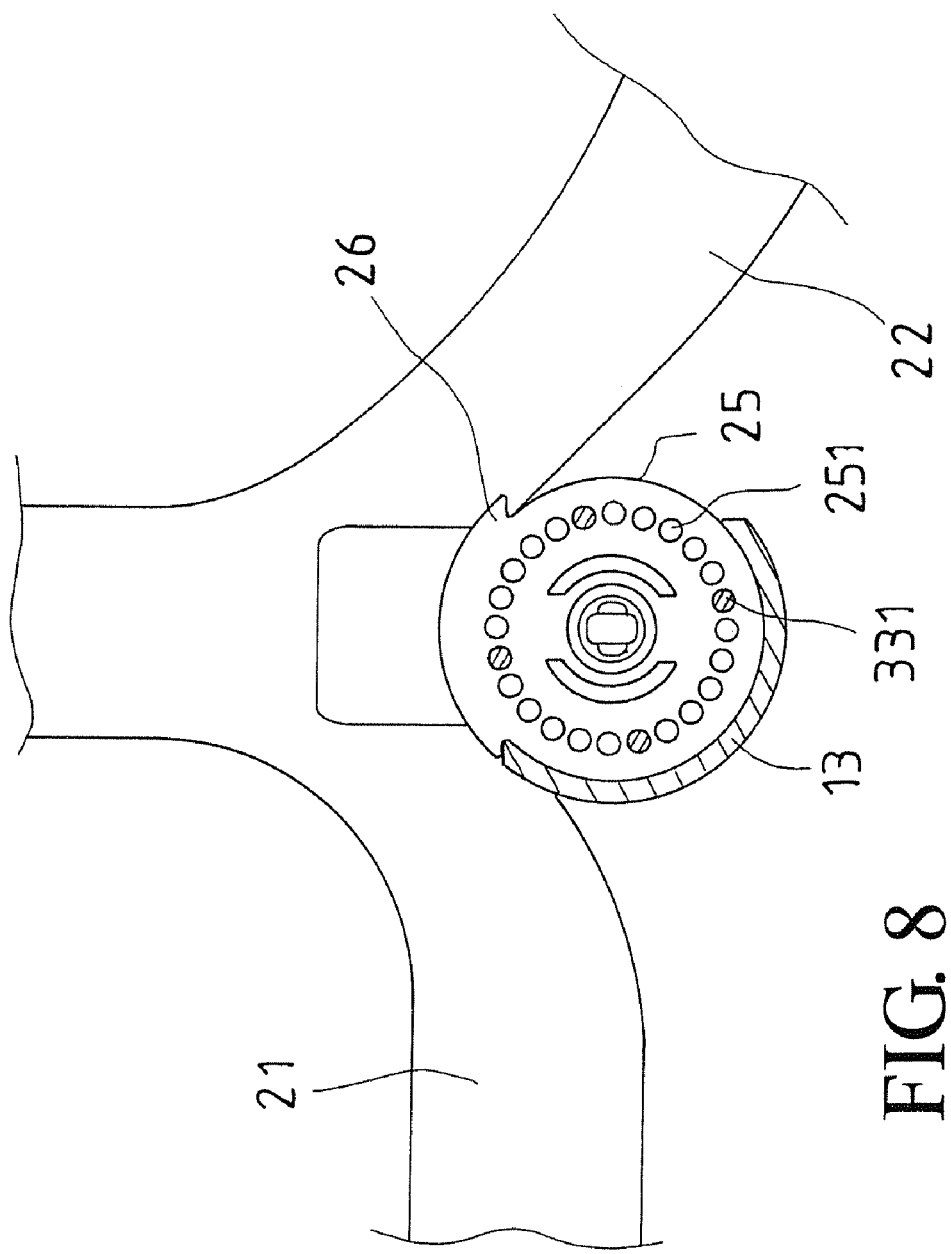
FIG. 8 is a schematic drawing a cross section of an upper limit curved part and a lower limit curved while a mask body is lifted according to the present invention.
Figure 9:
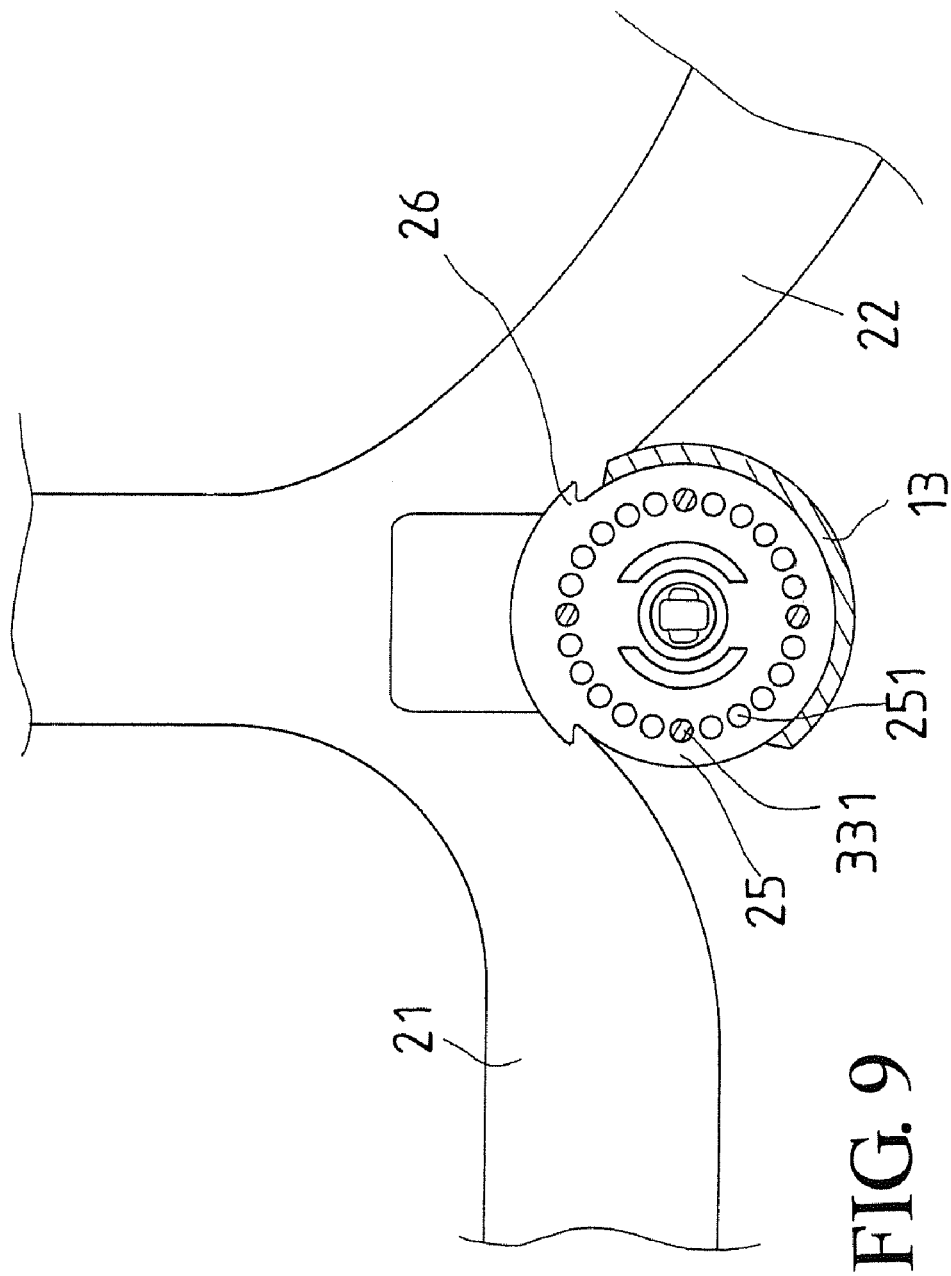
FIG. 9 is a schematic drawing a cross section of an upper limit curved part and a lower limit curved while a mask body is pulled down according to the present invention.

Furthermore, refer to FIG. 8 and FIG. 9, a lower limit curved part 13 is formed around the insertion hole 111 on the inner side of the hollow frame 11 and an upper limit curved part 26 corresponding to the lower limit curved part 13 is arranged between the positioning ring 25 and the curved part 21. Thus the mask body 1 is pivoted within a certain range between two ends of the upper limit curved part 26. In this embodiment, the mask 1 can be pivoted up to 90 degrees. By the projecting block 331 of the positioning disc 33 assembled with the hole 251 of the positioning ring 25, the mask body 1 can be pivoted in multiple stages. And there is a fixed point per each 15 degree. Thus the mask body 1 can be pivoted and rotated to an angle required more conveniently.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalent.

What is claimed is:

1. A protective mask comprising: a mask body, a hoop, two angle adjustment members and a head size adjustment device; wherein the mask body includes a hollow frame curved inward and disposed with an insertion hole on a left side and a right side thereof correspondingly, and a lens arranged at an concave area of the hollow frame;

the hoop that is received in the hollow frame and a curved part that is disposed on a front end of the hoop; two head circumference pieces extend horizontally from two ends of the curved part respectively; a slot is set on a rear end of each head circumference piece and a plurality of locking teeth is arranged at one side of each slot; a fastening segment and a corresponding adjustment segment are extending upwards from two ends of the curved part respectively; by the fastening segment and the adjustment segment fastened with each other, a space inside the hoop for receiving an user's head is adjusted; a positioning ring corresponding to the insertion hole is disposed projectingly on each of two ends of the curved part; the mask body is pivoted to the hoop by the two positioning rings and a plurality of holes is arranged around an outer surface of each positioning ring;

each of the two angle adjustment members is inserted through the insertion hole of the mask body and the positioning ring of the hoop so that a pivot angle of the mask body is adjusted by rotation of the angle adjustment member; the angle adjustment member includes a side knob, a projective pivot shaft arranged at an inner side of the side knob and passing through both the insertion hole and the positioning ring, an elastic part disposed around the pivot shaft, a positioning disc with a plurality of projecting blocks around a circumference on an outer surface thereof, and a fixing block connected to the pivot shaft for placing the elastic part and the positioning disc around the pivot shaft;

the head size adjustment device is rotated and fixed on the slots of the head circumference pieces and is including an inner housing, a first disc, an elastic element, a second disc, an outer housing and a rear knob; a shaft that passes through the slot is disposed on an outer surface of the inner housing; ratchet teeth engaged with the locking teeth are arranged at an inner surface of the first disc and a first projection for receiving the shaft is disposed on an outer surface of the first disc; the elastic element is placed around the first projection and then together with the first projection to be mounted and locked into the second disc; a second projection being assembled with the rear knob is set on an outer surface of the second disc and a plurality of positioning bumps is disposed around the circumference of the second disc; the outer housing and the inner housing are assembled with each other; a third disc with a plurality of concaves arranged circularly thereof is arranged at an outer surface of the outer housing and the concaves are corresponding to and engaged with the positioning bumps.

2. The protective mask as claimed in claim 1, wherein a locking block is disposed on one side of the fastening segment while the adjustment segment is arranged with a plurality of locking holes and a groove on a rear end thereof; the locking block is locked with the locking hole and the fastening segment is inserted through the groove.

3. The protective mask as claimed in claim 1, wherein a lower limit curved part is set around the insertion hole on an inner side of the hollow frame and an upper limit curved part corresponding to the lower limit curved part is arranged between the positioning ring and the curved part so that the mask body is pivoted within a range between two ends of the upper limit curved part.

* * * * *